United States Patent [19]
Theriault

[11] Patent Number: 5,357,644
[45] Date of Patent: Oct. 25, 1994

[54] ADJUSTABLE TOOTHBRUSH

[76] Inventor: Bertrand R. Theriault, 26 Ouellet Street, Edmundston, N.B., Canada, E3V 3H9

[21] Appl. No.: 100,384

[22] Filed: Aug. 2, 1993

[51] Int. Cl.$^5$ ................ A46B 13/02; A46B 13/08; A61C 17/34
[52] U.S. Cl. .................... 15/22.1; 15/167.1; 15/201
[58] Field of Search .............. 15/22.1, 167.1, 201, 15/203

[56]  References Cited
U.S. PATENT DOCUMENTS

| | | | |
|---|---|---|---|
| 696,798 | 4/1902 | Chambers | 15/203 |
| 1,517,320 | 12/1924 | Stoddart | 15/22.1 |
| 1,592,510 | 7/1926 | Toepperwein | 15/203 |
| 4,545,087 | 10/1985 | Nahum | 15/22.1 |
| 4,989,287 | 2/1991 | Scherer | 15/22.1 |

FOREIGN PATENT DOCUMENTS

| | | | |
|---|---|---|---|
| 152193 | 4/1903 | Fed. Rep. of Germany | 15/203 |
| 1166163 | 6/1958 | France | 15/22.1 |

Primary Examiner—David A. Scherbel
Assistant Examiner—Mark Spisich

[57] ABSTRACT

An adjustable toothbrush where the user can select, by turning a thumb knob on the brush handle, the inclination of the bristles to thereby improve on the cleaning of those hard to reach areas of the dentition. The toothbrush comprises a handle, a hollow brush body, a plurality of bristle bundles having their base moulded into resilient holders, a cam plate, a thumb knob connected to a cam shaft and a brush body cover. The cam plate slides within the hollow brush body and the brush body cover in a plane perpendicular to the bristles, and under the action of the thumb knob. The cam plate has a plurality of cavities for receiving the end of the bristle holders. Thus the movement of the cam plate is transmitted to all bristles in harmony.

20 Claims, 8 Drawing Sheets

ADJUSTABLE TOOTHBRUSH

BACKGROUND OF THE INVENTION

The invention relates to a toothbrush having adjustable orientation of the bristles to better adapt to the part of the dentition being cleaned.

The best cleaning result with all toothbrushes is obtained by maintaining the placement of the brush so that the bristles make a right angle with the surface of a tooth, thereby keeping the ends of the bristles in contact with the tooth surface.

In an ordinary toothbrush, the orientation of the bristles is fixed, and the handle is rigid. It is relatively easy to brush the foremost teeth. However, the limitation of the handle movement by the opening of the mouth, makes it harder to maintain ideal bristles orientation on the rear teeth. The rear teeth are often brushed with the side of curved bristles, thereby limiting the abrasion and the reach of the brushing. The inconveniences of the fact with ordinary toothbrushes are that gaps between teeth, hidden surfaces, and low spots on teeth surface are often left uncleaned.

SUMMARY OF THE INVENTION

It is an object of this invention to provide a toothbrush where the user can select, by turning a thumb knob on the brush handle, the inclination of the bristles to thereby improve on the cleaning of those hard to reach areas of the dentition.

Accordingly, the toothbrush comprises a handle, a hollow brush body, a plurality of bristle bundles, a cam plate, a thumb knob connected to a cam shaft and a brush body cover.

The end of each bundle of bristles is moulded into a resilient holder. The holders are held in individual holes in the wall of the hollow brush body, The wall of the hollow brush body having a thickness of much less than the length of the holder, there is a substantial portion of the holder which extends inside the brush body. The mounting of the holder to the brush body acting as a pivot, it is possible to incline the bundle by pushing sideways upon the free end of the holder.

The cam plate slides within the hollow brush body and the brush body cover, in a plane perpendicular to the bristles. The cam plate has a plurality of cavities for receiving the free ends of all bundles. Thus, the movement of the cam plate is transmitted to all bristles at the same time.

The end of the cam plate near the handle has a hole for pivoting on the cam shaft. The cam shaft is connected to the thumb knob, and is held in place into an upper thumb knob socket in the brush handle, and in a lower thumb knob socket in the brush body cover. The angular positioning of the thumb knob changes the orientation of the cam shaft, and thereby changes the position of the cam plate within the brush body.

The longitudinal movements of the cam plate, to deflect the bristles in the forward or rearward direction, is guided by the cam shaft, and by two bosses, one protruding inwardly from each respective side of the hollow brush body.

The bosses, acting as fulcrums, also transmit lateral displacements of the thumb knob into lateral inclination of the bristles. Therefore, a full rotation of the thumb knob results in a full rotation of the ends of the bristles.

The leverage obtained from the action of the cam makes it easy to adjust the orientation of the bristles to any inclination with very little force on the thumb knob. This inclination is maintained without holding the thumb knob, despite vigorous working of the bristles.

It is also an object of this invention to provide an electrically driven version of the manual toothbrush where the rotation of the cam shaft, is activated by a gearing system and an electric motor to provide continuous oscillation of the bristles.

A preferred embodiment of the invention will now be described by way of examples, with references to the accompanying drawings.

A BRIEF DESCRIPTION OF THE DRAWINGS

The accompanying drawings, which are incorporated in and form a part of the specification, illustrate the invention and, together with the detailed description, serve to explain the principles of the invention. In the drawings;

FIG. no. 1 illustrates a side view of the toothbrush.

FIG. no. 2 shows a view of the toothbrush facing the bristles.

FIG. no. 3 is an exploded side view of the invention, showing the mounting of the components.

FIG. no. 4 shows a top view of the thumb knob.

FIG. no. 5 is a side view of the thumb knob, and the cam shaft.

FIG. no. 6 is a cross section of the cam shaft along line 6 of FIG. no. 5. The figure illustrates the profile of the cam lobe in relation to the axis of rotation.

FIG. no. 7 is a cross section of the hollow brush body, showing the position of the cam plate when the thumb knob is in the rightmost position.

FIG. no. 8 is a cross section of the hollow brush body, a long the line 8 of FIG. no. 7.

FIG. no. 9 is a cross section of the hollow brush body, showing the position of the cam plate when the thumb knob is in the leftmost position.

FIG. no. 10 is a cross section of the hollow brush body, along line 10 of FIG. no. 9.

FIG. no. 11 is a cross section of the hollow brush body, showing the position of the cam plate when the thumb knob is in the farmost position.

FIG. no. 12 is a cross section of the hollow brush body, along line 12 of FIG. no. 11.

FIG. no. 13 is a cross section of the hollow brush body, showing the position of the cam plate when the thumb knob is in the nearmost position.

FIG. no. 14 is a cross section of the hollow brush body, along line 14 of FIG. no. 13.

FIG. no. 15 is an enlarged view of FIG. no. 12 to better illustrate the action of the cam plate with the thumb knob in the farmost position.

FIG. no. 16 is an enlarged view of FIG. no. 14 to better illustrate the action of the cam plate with the thumb knob in the nearmost position.

FIG. no. 17 is an enlarged detail of FIG. no. 16.

FIG. no. 18 illustrates a cam plate which has a round hole for following all movements of the cam shaft.

FIG. no. 19 shows a cam plate which has a longitudinal slot for following only the lateral movements of the cam shaft.

FIG. no. 20 shows another version of a cam plate which has a transverse slot for following only the longitudinal movements of the cam shaft.

FIG. no. 21 illustrates another version of a cam plate for activating only two rows of bristles in a four rows brush.

FIG. no. 22 shows aversion of the invention which has a cam plate and a brush body curved rearwardly.

FIG. no. 23 shows another version of the invention which has a cam plate and a brush body curved forwardly.

FIG. no. 24 shows an automatic version of the invention with a handle large enough to contain an electric motor, a gearing system and a battery.

FIG. no. 25 is a cross section of the handle along line 25 of FIG. no. 24. The figure illustrates the gearing system connected to the cam shaft.

DETAILED DESCRIPTION OF THE INVENTION

Figures 1, 2:
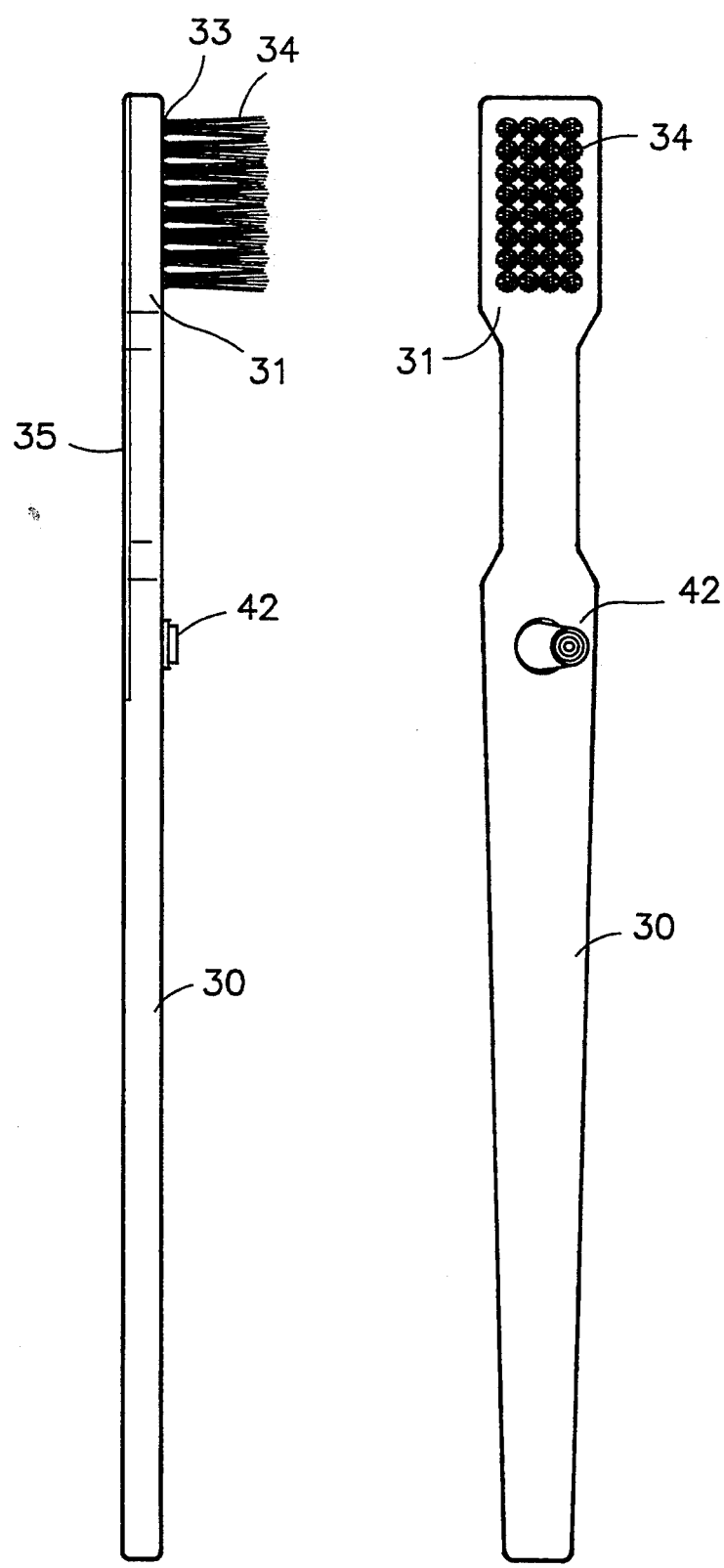
Figure 3:
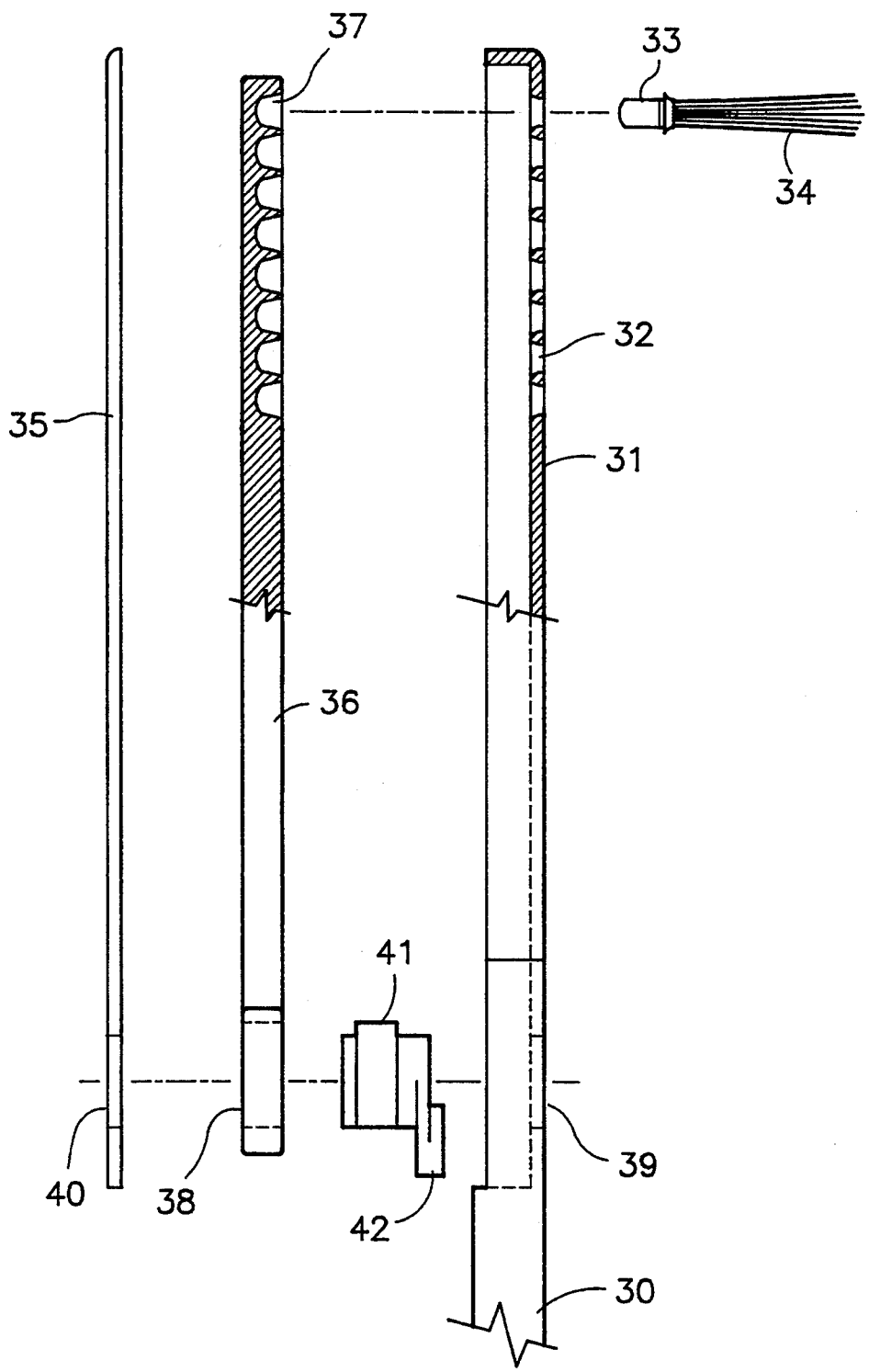
Figure 4:
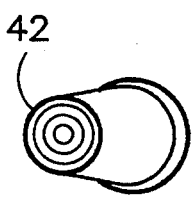
Figure 5:
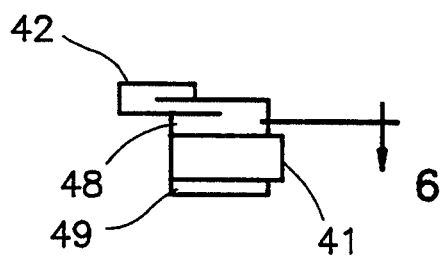
Figure 6:
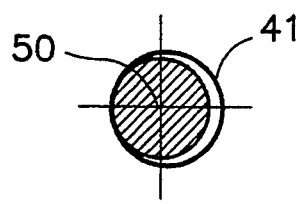
Figures 7, 8:
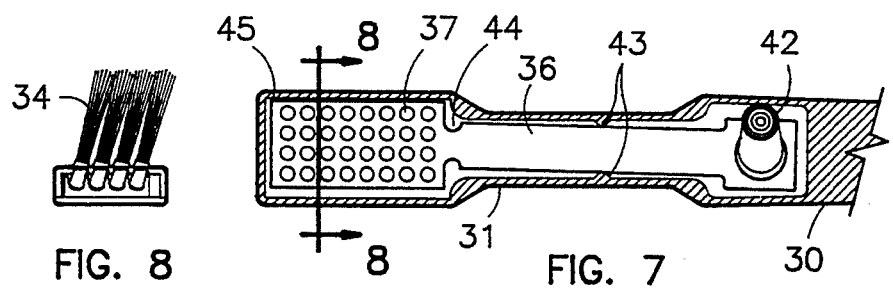
Figures 9, 10:
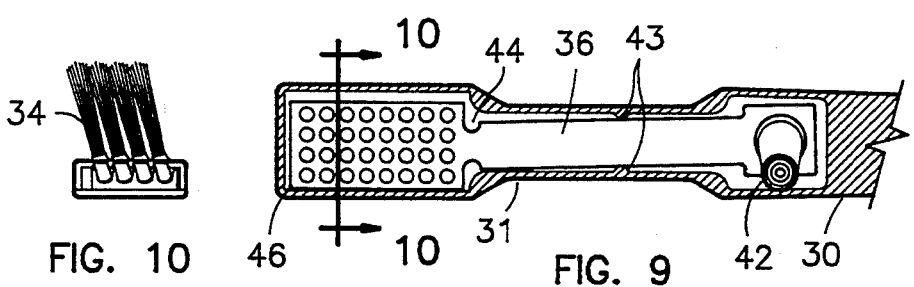
Figure 11:
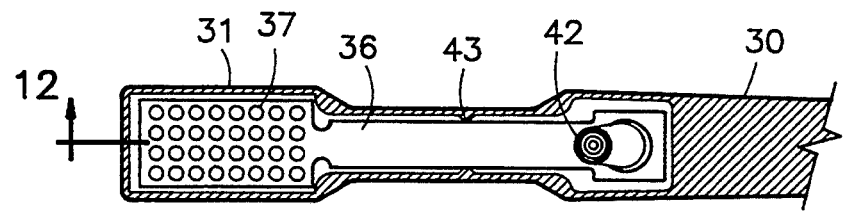
Figure 12:
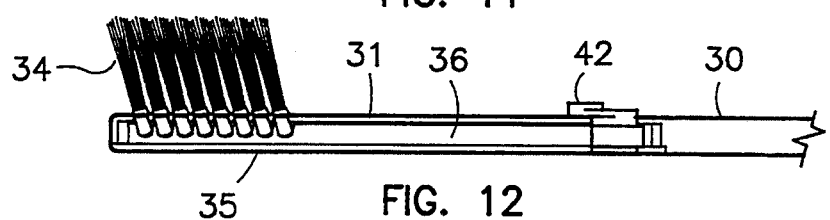
Figure 13:
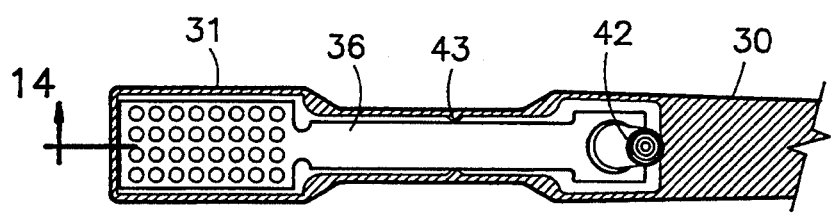
Figure 14:
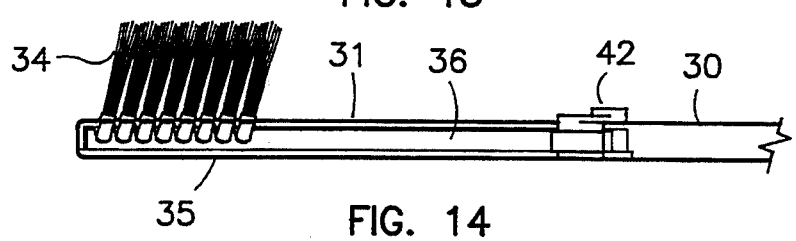
Figure 15:
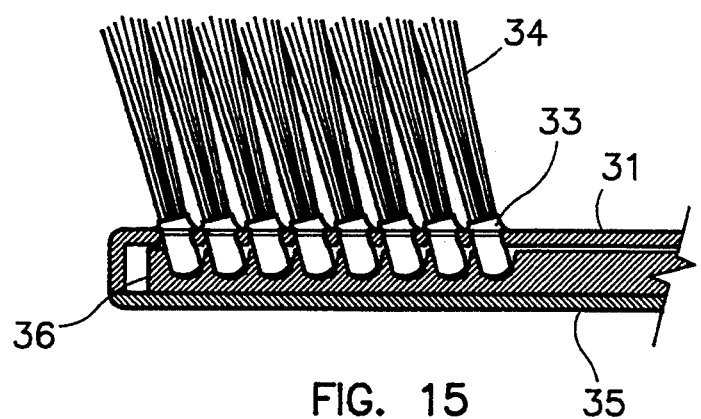
Figure 16:
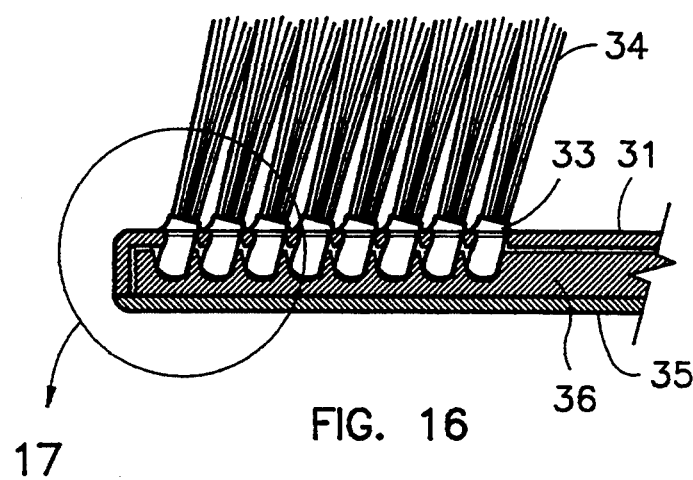
Figure 17:
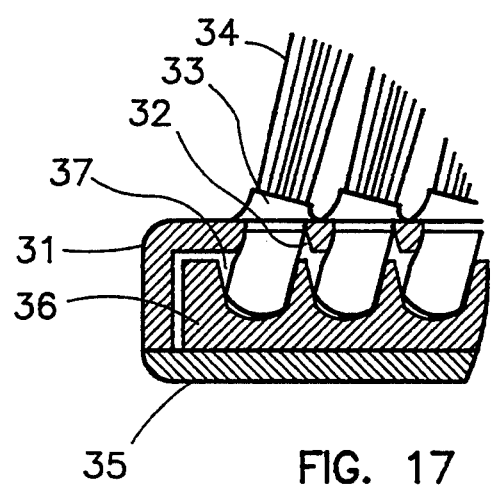
Figure 18:
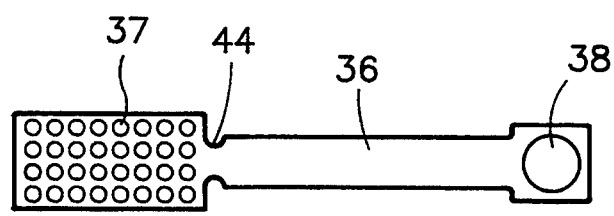
Figure 19:
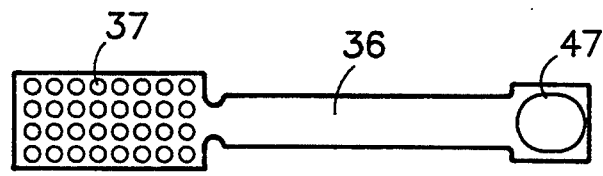
Figure 20:
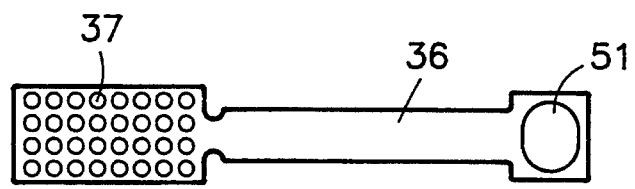
Figure 21:
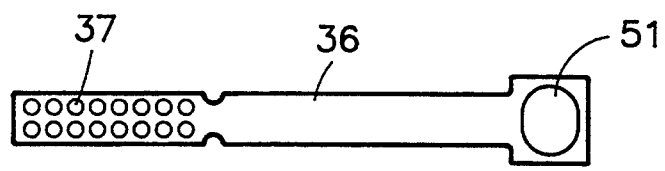
Figures 22, 23:
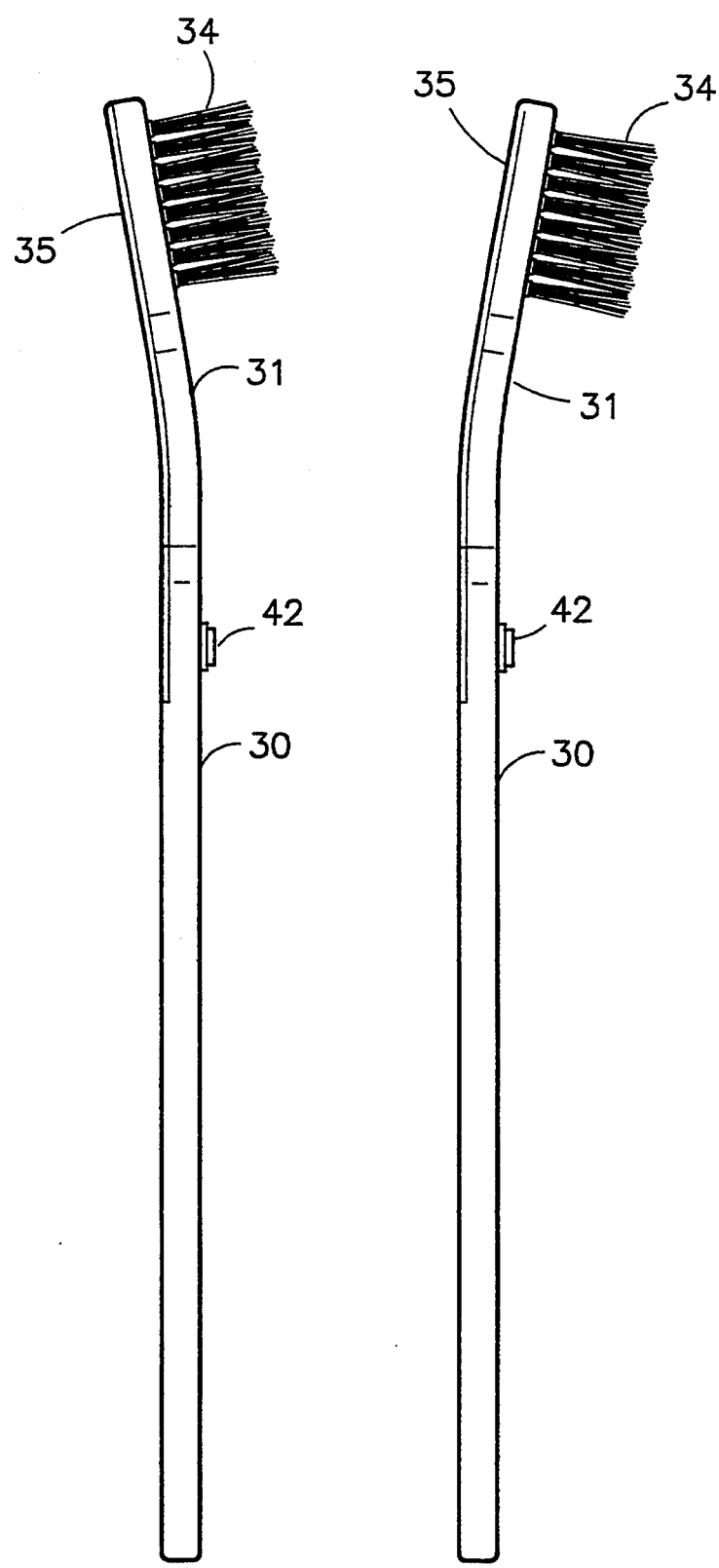

Referring to FIGS. no. 1, 2 and 3, the adjustable toothbrush comprises a handle 30, a hollow brush body 31, a plurality of bristles bundles 34, a cam plate 36, contained within the hollow brush body 31, and held in place by a brush body cover 35, and a cam shaft 41 connected to a thumb knob 42.

The end of each bundle of bristles 34 is moulded into a resilient holder 33. The holders 33 are glued into holes 32, in the wall of the hollow brush body 31. The cam plate 36 has a plurality of cavities 37 to receive the ends of the resilient holders 33 protruding inside the hollow brush body 31.

One end of the cam plate 36 has a hole 38 for fitting slidably over the cam shaft 41.

The cam shaft 41 is held in place and is free to rotate within an upper socket 39 in the upper wall of the hollow brush body 31, and within a lower socket 40 in the brush body cover 35. Referring to FIGS. no. 3, 4, 5 and 6, the upper portion 48 of the cam shaft rotates in the upper socket 39, and the lower portion 49 of the cam shaft rotates in the lower socket 40. The rotation of the thumb knob 42 causes the centre of the cam 41 to circulate about the axis 50 of both sockets 39, 40.

The movement of cam 41 is therefore transmitted to the cam plate 36 through hole 38.

Referring to FIGS. no. 7, 8, 9 and 10, the dimensions of the void inside the hollow brush body 31 is slightly larger than the dimensions of the cam plate 36, thus allowing movement of cam plate 36 within a plane perpendicular to a neutral central axis of resilient holder 33.

A pair of bosses 43 protruding inside of the hollow brush body 31 provides fulcrums to transmit the lateral displacement of the thumb knob 42 into lateral displacement of the cam plate 36 and thus into transverse inclination of the bristles 34.

A reduction 44 in the cross section of the cam plate 36 provides a weak point for bending and aligning the cam plate 36 within the hollow brush body 31, under the reaction of corner 45 or 46 touching the inside wall of the hollow brush body 31, during lateral displacements.

Similarly, the longitudinal displacements of the thumb knob 42, as seen on FIGS. no. 11, 12, 13 and 14 result in forward and rearward deflections of the bristles.

The major advantage of using a cam 41 is that, once a bristle inclination is selected, the working of the bristles 34 during use of the toothbrush is not sufficient to force the thumb knob 42 out of position.

The mounting of the resilient holders 33 into holes 32 in the wall of the hollow brush body 31 is better seen on FIGS. no. 15, 16 and 17. The conical shape of the cavities 37, for acting upon the resilient holders 33 without binding, is also better illustrated on FIG. no. 17.

This description of the invention shall not constitute a limitation in the scope of its applications. Also it shall not constitute a limitation in the possible configuration of its elements.

Several other versions of the invention can be built. As a comparison, FIG. no. 18 illustrates the cam plate 36 as described in the invention, which has a circular hole 38 to follow all movements of the cam shaft 41. In this case, it is possible to incline the bristles in any directions according to any angular position of the thumb knob 42.

Conversely, FIG. no. 19 shows a cam plate 36 having a longitudinally oriented oblong hole 47 for transmitting only the lateral displacement of the cam shaft 41. Furthermore, a transversally oriented oblong hole 51 as shown on FIG. no. 20 transmits only the longitudinal displacement of the cam shaft 41.

The cam plate 36 can also be manufactured with 2 rows of cavities 37, as illustrated on FIG. no. 21. The advantage of this arrangement is to maintain minimum width of the hollow brush body 31, and still deflecting the centre rows of a typical four rows brush.

The configuration of the cam plate 36, when made with a plastic material, permits some flexibility in a direction perpendicular to the plane of movement, while maintaining enough rigidity for the intended functions. The flexion permissible allows a certain level of curvature in the hollow brush body 31, and the creation of curved models as shown on the FIGS. no. 22 and 23.

Figures 24, 25:
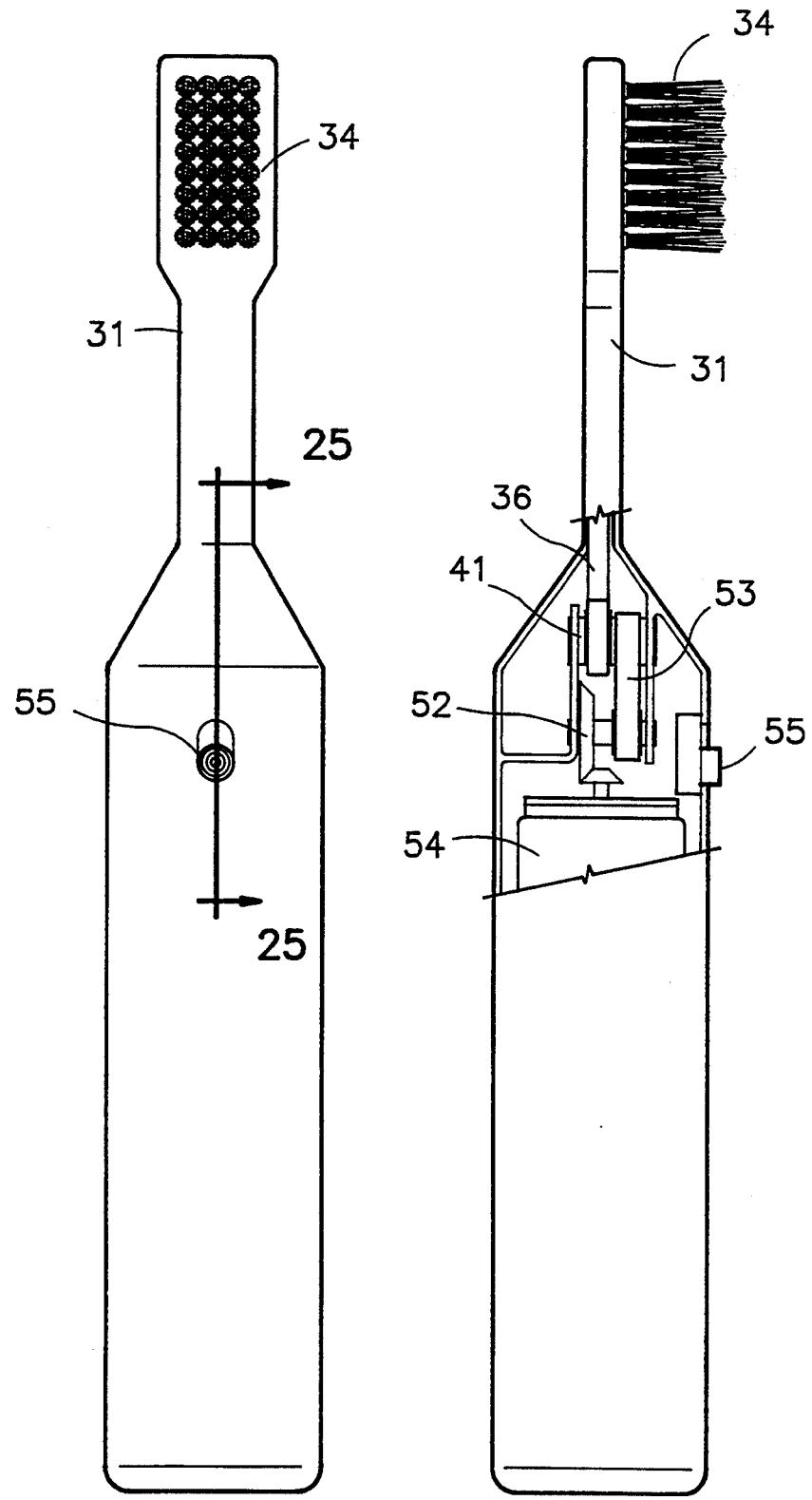

Another embodiment of the invention is illustrated on FIGS. 24 and 25. The cam plate 36 and the cam shaft 41 as previously described are activated by a belt system 53, a gearing system 52 and an electric motor 54. In this case the conventional thumb knob is replaced by an on-off switch 55 for the motor. This model provides a continuous rotation of the cam shaft 41, and thus a continuous circular oscillation of the end of the bristles 34, for maximum cleaning efficiency.

The embodiments of the invention in which an exclusive property or privilege is claimed are defined as follows:

1. A toothbrush having:
   an elongated handle,
   a hollow brush body having;
      an elongated exterior surface extending from and parallel to the longitudinal axis of said handle, said exterior surface being adapted to receive a plurality of spaced apart bristle bundles, and
      an elongated interior space forming the hollow portion of said body, said hollow portion having at least one guiding surface defining a longitudinal direction parallel to said longitudinal axis and a transverse direction, and at least two fulcrum means, said fulcrum means being mounted transversely to said guiding surface, and on opposite sides of said interior space,
   a plurality of spaced apart bristle bundles, each said bristle bundle having a free end, a mounting end, a neutral central axis defined by the bristles of the respective bristle bundles, and a holder covering said mounting end, each said holder being defined by a base, wherein each said holder is locally mounted adjacent said exterior surface with a part of each said holder extending within said hollow portion, and wherein said neutral central axis of each of said bundles is substantially perpendicular to said guiding surface when said bristle bundles are oriented perpendicular to said exterior surface, an elongated cam plate mounted within said hollow portion, said cam plate having a drive end and a driven end, said cam plate having dimensions smaller than the dimensions of said hollow portion, said cam plate being linearly movable longitudinally within said hollow portion and following said guiding surface, said cam plate also being movable transversely following said guiding surface, and said cam plate also having a pivotal movement, wherein said pivotal movement is effected by levering said cam plate over said fulcrum means.

said driven end of said cam plate having a plurality of spaced apart cavities, each said cavity is adapted to receive a respective one of said bases, such that a movement of said cam plate is transmitted to said bristle bundles in harmony, a cam mounted within said hollow portion, and adapted for rotation about a fixed axis, said fixed axis being perpendicular to the longitudinal direction of movement of said cam plate, a cam actuating means to effect a rotational displacement of said cam, a connecting means on said drive end of said cam plate to transmit said rotational displacement of said cam to said cam plate, whereby a longitudinal component of a displacement of said cam is ultimately transmitted directly to said bases of said holders, and a transverse component of a displacement of said cam is ultimately transmitted indirectly, over said fulcrum means, to said bases of said holders, and whereby a relative movement of each said base of each said holder with respect to a respective mounting location of each said holder at said exterior surface causes said bristle bundles to deflect from their respective neutral central axis, in a direction relative to an angular position of said cam.

2. A toothbrush as claimed in claim 1 wherein said fulcrum means act upon a central portion of said cam plate such that said a displacement of said cam actuating means is proportionally transmitted to said bases of said holders.

3. A toothbrush as claimed in claim 1 wherein said fulcrum means are two bosses.

4. A toothbrush as claimed in claim 1 wherein said holders are made of a resilient material.

5. A toothbrush as claimed in claim 1 wherein said cam actuating means is an externally mounted manually actuatable control means.

6. A toothbrush as claimed in claim 5 wherein said manually actuatable control means is a thumb knob offset from said fixed axis.

7. A toothbrush as claimed in claim 1 wherein said connecting means is a hole through said cam plate, encompassing said cam.

8. A toothbrush as claimed in claim 7 wherein said hole is circular.

9. A toothbrush as claimed in claim 7 wherein said hole is an oblong hole, oriented along the longitudinal axis of said cam plate, said oblong hole having a width substantially the same distance as a diameter of said cam, and a length greater than a diameter of said cam, whereby said movement of said cam actuating means is selectively transmitted to said bases of said holders.

10. A toothbrush as claimed in claim 7 wherein said hole is an oblong hole, oriented along the transverse direction of movement of said cam plate, said oblong hole having a width substantially the same distance as a diameter of said cam, and a length greater than a diameter of said cam, whereby said movement of said cam actuating means is selectively transmitted to said bases of said holders.

11. A toothbrush as claimed in claim 1 wherein said cam plate has a segment along its length reduced in cross-section, said segment being located between said drive end and said driven end, said segment providing a weak point such that flexion about said weak point is possible, whereby said flexion cooperatively associated with a confinement of said cam plate within said hollow portion causes all said cavities to follow a substantially parallel transverse displacement despite an arcuate movement of said connecting means, when said cam plate is levered over one said fulcrum means.

12. A toothbrush as claimed in claim no. 1 wherein said plurality of cavities are less in number than said plurality of bristle bundles such that only a portion of said plurality of bristle bundles are deflected from their neutral central axis.

13. A toothbrush as claimed in claim 1 wherein said cam acting upon said cam plate, in combination with said cam plate acting upon said holders of bristle bundles represent a substantial mechanical advantage, such that a vigorous working of the bristles is not sufficient to effect a displacement of said cam actuating means from a selected position.

14. A toothbrush as claimed in claim no. 1 wherein said cam plate, and said hollow brush body are curved.

15. A toothbrush as claimed in claim no. 1 wherein said cam actuating means is a gearing system and an electric motor, whereby a continuous rotation of said motor causes a deflection of said bristle bundles from their neutral central axis to continuously change, following a circular motion around said neutral central axis.

16. An adjustable toothbrush comprising;
an elongated handle,
a hollow brush body having;
  a flat surface extending from and parallel to the longitudinal axis of said handle, said flat surface defining a longitudinal direction and a transverse direction, said flat surface having a plurality of regularly spaced apart holes, said flat surface having two side edges and an end edge,
  two side surfaces, each said side surface joining with said flat surface at a respective said side edge,
  one end surface joining with said flat surface at said end edge,
  said flat surface, said side surfaces, and said end surface defining an inner zone of said hollow brush body,
a brush body cover being substantially parallel to, and having substantially the same dimensions of, said flat surface, joining with said side surfaces and said end surface, such that said inner zone is completely enclosed,
a plurality of bristle bundles, each defining a neutral central axis pointing in a direction substantially perpendicular to said flat surface when said bundles are oriented perpendicular to said flat surface, each said bundle having one end moulded in a resilient holder, each said holder being held in a respective hole in said flat surface, such that a substantial part of said holder extends within said inner zone, said part of said holder extending within said inner zone being defined by a base of said holder, an elongated cam plate having dimensions smaller than the dimensions of said inner zone, each that a movement of said cam plate within said inner zone and along said flat surface is possible, said cam plate having a drive end and a driven end, said drive end having an opening, a cam shaft pivoted between and about a fixed axis perpendicular to said flat surface and said brush body cover, said cam shaft having a cam lobe for turning within and being encompassed by said opening of said drive end, an externally mounted thumb knob connected to said cam shaft, providing the means for changing the angular position of said cam lobe within said opening, and therefrom, for selecting the relative position of said drive end within said inner zone, said side surfaces having each a boss protruding transversely towards said inner zone, said cam plate being guided within said hollow brush body between said bosses, the longitudinal component of a displacement of said cam lobe is transmitted directly to said driven end, said cam plate being also levered over said bosses, the transverse component of a displacement of said cam lobe is transmitted indirectly to said driven end, accordingly, all angular displacements of said cam lobe are ultimately transmitted proportionally to said driven end, said driven end has a plurality of regularly spaced apart cavities, whereby each cavity is adapted to receive a respective one of said bases, whereby a displacement of said cam plate is transmitted to all said bases of said holders, and whereby a relative movement of each said base of each said holder with respect to a respective mounting location of each said holder at said flat surface causes said bristle bundles to deflect from their respective neutral central axis.

17. An adjustable toothbrush as claimed in claim 16 wherein said opening is circular, having a diameter corresponding to a diameter of said cam lobe, such that all movements of said cam lobe are transmitted to said driven end.

18. An adjustable toothbrush as claimed in claim 16 wherein said opening is an oblong hole oriented along the longitudinal axis of said cam plate, said oblong hole having a width substantially the same distance as a diameter of said cam lobe, and a length greater than a diameter of said cam lobe, whereby only the transverse component of an angular displacement of said cam lobe is transmitted to said driven end.

19. An adjustable toothbrush as claimed in claim 16, wherein said opening is an oblong hole oriented along a transverse axis of said cam plate, said oblong hole having a width substantially the same distance as a diameter of said cam lobe and a length greater than a diameter of said cam lobe, whereby only the longitudinal component of an angular displacement of said cam lobe is transmitted to said driven end.

20. An adjustable toothbrush as claimed in claim 16 wherein said cam lobe acting upon said cam plate in combination with said cam plate acting upon said holders of bristle bundles represent a substantial mechanical advantage, such that a vigorous working of the bristles is not sufficient to effect a displacement of said thumb knob from a selected position.

* * * * *